(12) United States Patent
Kim et al.

(10) Patent No.: US 9,028,885 B2
(45) Date of Patent: May 12, 2015

(54) **COMPOSITION FOR PROMOTING ADIPOCYTE DIFFERENTIATION CONTAINING AN EXTRACT OF *REHMANNIA GLUTINOSA*, LICORICE, COICIS SEMEN, HORDEI FRUCTUS, CHAENOMELIS FRUCTUS, ACANTHOPANACIS CORTEX OR PUERARIAE RADIX**

(75) Inventors: Ji Seong Kim, Yongin-si (KR); Ga Young Cho, Cheongju-si (KR); Eun Joo Kim, Suwon-si (KR); Jun Seong Park, Suwon-si (KR); Ho Sik Rho, Yongin-si (KR); Hye Yoon Park, Anyang-si (KR); Duck Hee Kim, Seoul (KR); Han Kon Kim, Suwon-si (KR)

(73) Assignee: Amorepacific Corporation, Seoul (KR)

( * ) Notice: Subject to any disclaimer, the term of this patent is extended or adjusted under 35 U.S.C. 154(b) by 137 days.

(21) Appl. No.: 13/381,169

(22) PCT Filed: Jun. 30, 2010

(86) PCT No.: PCT/KR2010/004243
§ 371 (c)(1),
(2), (4) Date: Dec. 28, 2011

(87) PCT Pub. No.: WO2011/002223
PCT Pub. Date: Jun. 1, 2011

(65) Prior Publication Data
US 2012/0107427 A1    May 3, 2012

(30) Foreign Application Priority Data
Jun. 30, 2009   (KR) ........................ 10-2009-0058929

(51) Int. Cl.
| A61K 36/254 | (2006.01) |
| A61K 36/258 | (2006.01) |
| A61K 36/48 | (2006.01) |
| A61K 36/899 | (2006.01) |
| A61K 36/00 | (2006.01) |
| A61K 8/97 | (2006.01) |
| A61K 36/484 | (2006.01) |
| A61K 36/488 | (2006.01) |
| A61K 36/732 | (2006.01) |
| A61K 36/804 | (2006.01) |
| A61K 36/8994 | (2006.01) |
| A61Q 19/08 | (2006.01) |

(52) U.S. Cl.
CPC ................ *A61K 8/97* (2013.01); *A61K 36/254* (2013.01); *A61K 36/484* (2013.01); *A61K 36/488* (2013.01); *A61K 36/732* (2013.01); *A61K 36/804* (2013.01); *A61K 36/899* (2013.01); *A61K 36/8994* (2013.01); *A61Q 19/08* (2013.01); *A61K 2800/91* (2013.01)

(58) Field of Classification Search
None
See application file for complete search history.

(56) References Cited

U.S. PATENT DOCUMENTS

| 5,747,049 | A   | * | 5/1998  | Tominaga      | 424/401    |
| 6,878,378 | B1  | * | 4/2005  | Yamaki et al. | 424/401    |
| 2003/0072816 | A1 | * | 4/2003  | Hirao         | 424/725    |
| 2004/0223942 | A1 | * | 11/2004 | Fujimura      | 424/74     |
| 2005/0154066 | A1 | * | 7/2005  | Fujii et al.  | 514/690    |
| 2005/0220810 | A1 | * | 10/2005 | Yano et al.   | 424/195.17 |
| 2006/0018867 | A1 | * | 1/2006  | Kawasaki et al. | 424/70.122 |
| 2007/0020207 | A1 | * | 1/2007  | Kawasaki      | 424/62     |
| 2008/0292728 | A1 | * | 11/2008 | Kawasaki      | 424/661    |
| 2010/0273195 | A1 | * | 10/2010 | Fujimura      | 435/15     |

FOREIGN PATENT DOCUMENTS

| CN | 1277839 A | 12/2000 |
| CN | 1430499 A | 7/2003 |
| CN | 1713889 A | 12/2005 |
| CN | 101015514 A | 8/2007 |
| CN | 101360478 A | 2/2009 |
| JP | 06-024937 | 2/1994 |
| JP | 08-283172 | 10/1996 |
| JP | 09-315988 | 12/1997 |
| JP | 10-130162 | 5/1998 |
| JP | 2002-097149 | 4/2002 |
| JP | 2004-075573 | 3/2004 |
| JP | 2009-073777 | 4/2009 |
| JP | 2009-523785 | 6/2009 |
| KR | 10-2006-0087134 A | 8/2006 |
| KR | 10-2008-0065726 A | 7/2008 |
| WO | WO 2007/083868 A1 | 7/2007 |

OTHER PUBLICATIONS

International Search Report for International Application No. PCT/KR2010/004243 mailed Mar. 30, 2011 (Form PCT/ISA/210).
Office Action for Chinese Patent Application No. 201080038210.X (mailed Oct. 25, 2012).
Office Action for Japanese Patent Application No. 2012-517409 (mailed Jun. 24, 2014).

* cited by examiner

*Primary Examiner* — Chris R Tate
*Assistant Examiner* — Russell Fiebig
(74) *Attorney, Agent, or Firm* — Merchant & Gould

(57) ABSTRACT

Disclosed is a composition comprising an extract of at least one selected from a group consisting of *Rehmannia glutinosa*, licorice, Coicis Semen, Hordei Fructus, Chaenomelis Fructus, Acanthopanacis Cortex and Puerariae Radix as an active ingredient. The composition promotes adipocyte differentiation and lipid droplet formation and is effective in improving skin wrinkles, enhancing skin elasticity and preventing skin aging.

12 Claims, 2 Drawing Sheets

COMPOSITION FOR PROMOTING ADIPOCYTE DIFFERENTIATION CONTAINING AN EXTRACT OF *REHMANNIA GLUTINOSA*, LICORICE, COICIS SEMEN, HORDEI FRUCTUS, CHAENOMELIS FRUCTUS, ACANTHOPANACIS CORTEX OR PUERARIAE RADIX

This application is a U.S. National Stage Application under 35 U.S.C. §371 of International Patent Application No. PCT/KR2010/004243, filed 30 Jun. 2010, which claims the benefit of priority to Korean Patent Application No. 10-2009-0058929, filed 30 Jun. 2009, the disclosures of all of which are hereby incorporated by reference in their entireties. The International Application was published in Korean on 6 Jan. 2011 as WO 2011/002223. To the extent appropriate, a claim of priority is made to each of the above disclosed applications.

TECHNICAL FIELD

The present disclosure relates to a composition for promoting adipocyte differentiation and lipid droplet formation.

BACKGROUND

Adipocyte differentiation is a process by which preadipocytes become adipocytes wherein many external stimuli such as hormones and complex gene expressions are involved. Among the external signals inducing adipocyte differentiation, insulin is the best known hormone and plays a critical role in regulation of fat metabolism. Preadipocytes begin to differentiate into adipocytes in response to stimulation by insulin. Insulin also stores energy in the form of lipids via a complex mechanism involving increased glucose absorption and triglyceride synthesis, and promotes absorption of fatty acids derived from lipoproteins circulating in the bloodstream by activating lipoprotein lipase. The various actions of insulin in adipocytes are accompanied by increased transcription of genes regulated by insulin as well as phosphorylation of specific proteins and their fast activation. As the adipocyte differentiation is induced by insulin, transcription and expression of transcription factors such as PPARγ, C/EBP family, ADD1/SREBP1 or the like are increased, and the transcription factors induce the adipocyte differentiation through by triggering transcription one another.

Adipocyte differentiation occurs in the order of confluence, hormonal induction, clonal expansion, growth arrest and terminal differentiation. First, when preadipocytes are grown to confluence, growth arrest occurs at the G0/G1 cell cycle boundary. Given appropriate stimulation and expression of C/EBPβ and C/EBPδ, one or two rounds of cell division occur, which is known as clonal expansion. Before the preadipocytes are fully differentiated through expression of PPARγ and C/EBPα, they undergo growth arrest. In the last stage, i.e. in terminal differentiation, mature adipocytes are produced following continued growth arrest. The preadipocytes, which were similar to fibroblasts in the early stage of differentiation, become round in shape (morphological rounding-up). As mRNAs of lipoprotein lipase or the like are expressed, the transcription factors C/EBPβ and δ are transiently induced. Then, PPARγ and C/EBPα are expressed to regulate the genes that actually determine the phenotype of adipocytes or activate their expression. Those genes include glycerophosphate dehydrogenase (GPDH), acetyl-CoA carboxylase (ACC), malic enzyme (ME), glucose transporter type 4 (Glut 4), insulin receptor (IR), adipocyte selective fatty acid binding protein 2 (aP2) or the like. Through this process, lipid droplets are produced in the cytoplasm. They grow and unite with time to form one or more larger droplets.

If differentiation of human adipocytes can be promoted, and thus, if formation and accumulation of the lipid droplets can be promoted, skin wrinkling and elasticity can be improved.

SUMMARY OF THE INVENTION

Technical Problem

The present disclosure is directed to providing a composition for improving skin wrinkles, enhancing skin elasticity and preventing skin aging.

Technical Solution

In one general aspect, the present disclosure provides a composition for enhancing skin elasticity, comprising an extract of at least one selected from a group consisting of *Rehmannia glutinosa*, licorice, Coicis Semen, Hordei Fructus, Chaenomelis Fructus, Acanthopanacis Cortex and Puerariae Radix as an active ingredient.

In another general aspect, the present disclosure provides a composition for improving skin wrinkles, comprising an extract of at least one selected from a group consisting of *Rehmannia glutinosa*, licorice, Coicis Semen, Hordei Fructus, Chaenomelis Fructus, Acanthopanacis Cortex and Puerariae Radix as an active ingredient.

In another general aspect, the present disclosure provides a composition for preventing skin aging, comprising an extract of at least one selected from a group consisting of *Rehmannia glutinosa*, licorice, Coicis Semen, Hordei Fructus, Chaenomelis Fructus, Acanthopanacis Cortex and Puerariae Radix as an active ingredient.

In another general aspect, the present disclosure provides a composition for external skin application, comprising an extract of at least one selected from a group consisting of *Rehmannia glutinosa*, licorice, Coicis Semen, Hordei Fructus, Chaenomelis Fructus, Acanthopanacis Cortex and Puerariae Radix as an active ingredient.

Advantageous Effects

The composition according to the present disclosure, which contains an extract of at least one selected from a group consisting of *Rehmannia glutinosa*, licorice, Coicis Semen, Hordei Fructus, Chaenomelis Fructus, Acanthopanacis Cortex and Puerariae Radix as an active ingredient, provides the effects of enhancing skin elasticity, improving skin wrinkles and preventing skin aging by promoting adipocyte differentiation and lipid droplet formation. These effects can be better attained when the composition comprises a complex extract containing more than one of them.

The composition according to the present disclosure, which comprises an extract of at least one selected from a group consisting of *Rehmannia glutinosa*, licorice, Coicis Semen, Hordei Fructus, Chaenomelis Fructus, Acanthopanacis Cortex and Puerariae Radix as an active ingredient, may be used as a composition for external skin application.

DETAILED DESCRIPTION

Figure 1:
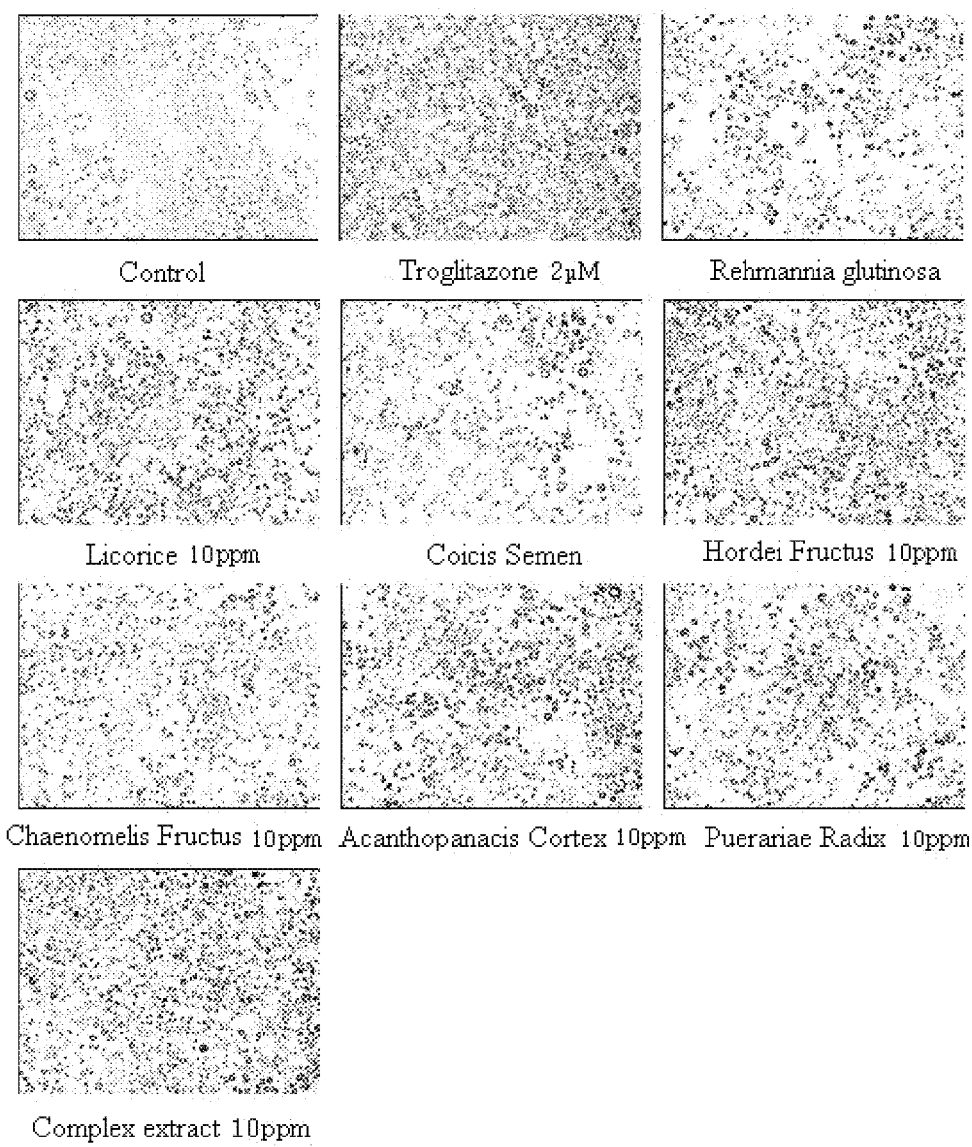
FIG. 1 shows a result of treating 3T3-L1 cells with an extract of *Rehmannia glutinosa*, licorice, Coicis Semen, Hordei Fructus, Chaenomelis Fructus, Acanthopanacis Cortex, Puerariae Radix or a complex extract thereof to induce differentiation, and staining with Oil Red O to confirm the formation of lipid droplets.

As used herein, the term "extract" includes any substance extracted from a natural product, regardless of the extraction method or the types of substances. For example, it includes an extract extracted from a natural product using a solvent such as water or an organic solvent, or a specific substance extracted from the natural product such as oil. As used herein, the term "complex extract" refers to a mixture containing two or more components. It includes a mixture containing two or more extracts or a mixture containing extract of two or more components.

As used herein, the term "skin" refers to the outer covering of an animal. The term is used in the broadest sense, including not only the face or body but also the scalp and hair.

Hereinafter, the present disclosure will be described in more detail.

In an aspect, the present disclosure provides a composition for enhancing skin elasticity, improving skin wrinkles or preventing skin aging, comprising an extract of at least one selected from a group consisting of *Rehmannia glutinosa*, licorice, Coicis Semen, Hordei Fructus, Chaenomelis Fructus, Acanthopanacis Cortex and Puerariae Radix as an active ingredient.

In another aspect, the present disclosure provides a composition for external skin application, comprising an extract of at least one selected from a group consisting of *Rehmannia glutinosa*, licorice, Coicis Semen, Hordei Fructus, Chaenomelis Fructus, Acanthopanacis Cortex and Puerariae Radix as an active ingredient.

*Rehmannia glutinosa* (*Rehmannia glutinosa*) is a perennial grass of the family Phrymaceae and is native to China. The root is thick and fleshy. It stretches sideways and is reddish brown. The stem is upright, 20-30 cm in height, and has hair. The leaves, which stem from the root, are clustered. They are oblong, with dull end and sharp stalk, saw-toothed at the edge. The surface of the leaf is wrinkled. Veins bulge at the back of the leaf and form networks. The leaves grow alternately on the stem. In the traditional medicine, the root is mainly used as herbal medicine as it is (raw), after being dried, or after being steamed and dried.

Licorice (*Glycyrrhiza uralensis*) is a perennial grass of the family Fabaceae. The reddish brown root stretches deep into the ground. The stem is angular and grows straight about 1 m. It looks gray-white because of dense white hair and has spreaded spots. The leaves grow alternately and are oddly pinnate. The small leaves are 7-17 in number, oval-shaped, and sharp at the end. The small leaf is 2-5 cm long and 1-3 cm wide. It has white hair and spots on both sides and is not saw-toothed. The flower blooms in July and August. The violet flower is 1.4-2.5 cm in length and racemiferous. It blooms at the leaf axil. The pod is thin, long and bent like a bow. It contains 6-8 kidney-shaped seeds. The sweet-tasting root is frequently used as medicine.

Coicis Semen refers to the seed of adlay (*Coix lacryma-jobi*) of the family Poaceae, with the hull removed. It is oval or broad oval. Both ends are a little concave. The backside is round and convex, and a deep, long groove is formed at the center. The backside is almost white and floury. The seed is enclosed with brown membranous shell and hull.

Hordei Fructus refers to grains of barley (*Hordeum vulgare*) germinated by controlling moisture, temperature and oxygen.

Chaenomelis Fructus refers to the oval or round fruit of quince (*Chaenomeles sinensis*). The immature fruit is green. As it ripens, the color changes to yellow and the surface becomes uneven. Although the fragrance is excellent, it tastes sour and astringent. The skin is hard and sticky because of oily components, which contribute to the fragrance and effect. It is native to China.

Acanthopanacis Cortex refers to the bark of the root, trunk or branches of *Acanthopanax sessiliflorum* of the family Araliaceae.

Puerariae Radix refers to the root of arrowroot (*Pueraria lobata*) with the peel removed.

In an aspect, the at least one selected from a group consisting of *Rehmannia glutinosa*, licorice, Coicis Semen, Hordei Fructus, Chaenomelis Fructus, Acanthopanacis Cortex and Puerariae Radix comprises one of each part of the corresponding plant. For example, the at least one selected from a group consisting of *Rehmannia glutinosa*, licorice, Coicis Semen, Hordei Fructus, Chaenomelis Fructus, Acanthopanacis Cortex and Puerariae Radix may comprise one of leaf, flower, stem, branch, root, fruit and seed of each plant.

In an aspect, the extract of at least one selected from a group consisting of *Rehmannia glutinosa*, licorice, Coicis Semen, Hordei Fructus, Chaenomelis Fructus, Acanthopanacis Cortex and Puerariae Radix may be prepared by a general extraction method. In an aspect, the extraction method may be a solvent extraction method. In an aspect, the solvent may be $C_1$-$C_5$ lower alcohol, ether, ethyl acetate, acetone or chloroform, although not being limited thereto. The $C_1$-$C_5$ lower alcohol may be, for example, one or more selected from a group consisting of methanol, ethanol, isopropyl alcohol, n-propyl alcohol, n-butanol and isobutanol.

In an aspect, the composition comprising an extract of at least one selected from a group consisting of *Rehmannia glutinosa*, licorice, Coicis Semen, Hordei Fructus, Chaenomelis Fructus, Acanthopanacis Cortex and Puerariae Radix as an active ingredient promotes differentiation of preadipocytes into adipocytes and increases the number and size of lipid droplets. By promoting adipocyte differentiation and lipid droplet formation and increasing skin density, the composition according to the present disclosure is effective in preventing skin wrinkles, enhancing skin elasticity and preventing skin aging. All the compositions comprising the individual extracts have such effects. The best effect can be achieved by a composition comprising the complex extract.

In an aspect, the composition comprising an extract of at least one selected from a group consisting of *Rehmannia glutinosa*, licorice, Coicis Semen, Hordei Fructus, Chaenomelis Fructus, Acanthopanacis Cortex and Puerariae Radix as an active ingredient may include the *Rehmannia glutinosa* extract, the licorice extract, the Coicis Semen extract, the Hordei Fructus extract, the Chaenomelis Fructus extract, the Acanthopanacis Cortex extract and the Puerariae Radix extract with a weight ratio of 20-30:1-10:20-30:1-10:1-10:5-15:20-30. When the composition contains the individual extracts with the aforesaid weight ratio, superior effect of promoting adipocyte differentiation and lipid droplet formation is achieved, and thus superior effect of enhancing skin elasticity, improving skin wrinkles or preventing skin aging can be attained. In another aspect, a composition comprising the complex extract of the *Rehmannia glutinosa* extract, the licorice extract, the Coicis Semen extract, the Hordei Fructus extract, the Chaenomelis Fructus extract, the Acanthopanacis Cortex extract and the Puerariae Radix extract as an active ingredient may comprise 25 wt % of the *Rehmannia glutinosa* extract, 5 wt % of the licorice extract, 24 wt % of the Coicis Semen extract, 6 wt % of the Hordei Fructus extract, 5 wt % of the Chaenomelis Fructus extract, 10 wt % of the Acanthopanacis Cortex extract and 25 wt % of the Puerariae Radix extract, based on the total weight of the complex extract.

In an aspect, the present disclosure provides a pharmaceutical composition containing a composition comprising an extract of at least one selected from a group consisting of *Rehmannia glutinosa*, licorice, Coicis Semen, Hordei Fructus, Chaenomelis Fructus, Acanthopanacis Cortex and Puerariae Radix as an active ingredient. The pharmaceutical composition may further comprise a pharmaceutical adjuvant such as preservative, stabilizer, wetting agent, emulsifier, salt for control of osmotic pressure, buffer, etc. or other therapeutically useful agents, and may be prepared into formulations for oral or parenteral administration according to methods known in the art.

Formulations for oral administration may include tablet, pill, granule, hard or soft capsule, powder, fine granule, dust, liquid, emulsion, syrup, pellet, or the like. These formulations may include, in addition to the active ingredient, a diluent (e.g., lactose, dextrose, sucrose, mannitol, sorbitol, cellulose or glycine) or a lubricant (e.g., silica, talc, stearic acid and its magnesium or calcium salt, or polyethylene glycol). A tablet may further include a binder such as magnesium aluminum silicate, starch paste, gelatin, tragacanth, methyl cellulose, sodium carboxymethyl cellulose or polyvinylpyrrolidone, as well as pharmaceutical adjuvants, e.g., a disintegrant such as starch, agar, and alginic acid or its sodium salt, an absorbent, a colorant, a flavor, a sweetener or the like. The tablet may be prepared by the commonly employed mixing, granulation or coating methods.

Formulations for parenteral administration may include an agent for external skin application, injection, lotion, ointment, gel, cream, suspension, emulsion, suppository, patch or spray, but are not limited thereto.

In an aspect, the pharmaceutical composition according to the present disclosure may be administered orally or parenterally, e.g., rectally, topically, transdermally, intravenously, intramuscularly, intraabdominally, subcutaneously, etc.

An administration dosage of the active ingredient will be different depending on the age, gender or body weight of a subject, the particular disease or pathological condition to be treated, severity of the disease or pathological condition, administration route or the discretion of a physician. The determination of the administration dosage considering these factors is within the level of those skilled in the art.

In another aspect, the present disclosure provides a beauty care composition containing a composition comprising an extract of at least one selected from a group consisting of *Rehmannia glutinosa*, licorice, Coicis Semen, Hordei Fructus, Chaenomelis Fructus, Acanthopanacis Cortex and Puerariae Radix as an active ingredient. The beauty care composition may be, for example, a cosmetic composition, and may comprise a cosmetically or dermatologically acceptable medium or base. It may be in any form appropriate for topical application, including, for example, solution, gel, solid, anhydrous paste, oil-in-water emulsion, water-in-oil emulsion, suspension, microemulsion, microcapsule, microgranule, ionic (liposome) or nonionic vesicular dispersion, foam, or aerosol further comprising compressed propellant. These compositions may be prepared according to the methods commonly employed in the art.

The beauty care composition may further comprise an adjuvant commonly used in the field of cosmetology or dermatology such as fat, organic solvent, solubilizer, thickener, gelling agent, emollient, antioxidant, suspending agent, stabilizer, foaming agent, aromatic, surfactant, water, ionic or nonionic emulsifier, filler, sequestering agent, chelating agent, preservative, vitamin, blocking agent, wetting agent, essential oil, dye, pigment, hydrophilic or lipophilic agent, lipid vesicle or any other ingredients commonly used in cosmetics. The adjuvant may be included in an amount generally used in the field of cosmetology or dermatology.

The formulation of the beauty care composition is not particularly limited but may be selected appropriately depending on the desired purposes. For example, it may be prepared into a formulation selected from a group consisting of nourishing lotion, astringent lotion, nourishing lotion, nourishing cream, massage cream, essence, eye cream, eye essence, cleansing cream, cleansing lotion, cleansing foam, cleansing water, pack, powder, concealer stick, body lotion, body cream, body oil, body essence, body cleanser, ointment, gel, patch and spray, but is not limited thereto.

The pharmaceutical or beauty care composition containing a composition according to the present disclosure may be applied to the face, particularly around the eyes or the mouth, cheek or forehead, neck, hands, feet or the like, without being limited thereto.

MODE FOR INVENTION

The preparation example and test examples will now be described. The following examples and experiments are for illustrative purposes only and not intended to limit the scope of the present disclosure.

Preparation Example

Extracts of *Rehmannia glutinosa*, licorice, Coicis Semen, Hordei Fructus, Chaenomelis Fructus, Acanthopanacis Cortex and Puerariae Radix were prepared according to the commonly employed extraction method. Then, a complex extract was prepared to contain 25 wt % of *Rehmannia glutinosa* extract, 5 wt % of licorice extract, 24 wt % of Coicis Semen extract, 6 wt % of Hordei Fructus extract, 5 wt % of Chaenomelis Fructus extract, 10 wt % of Acanthopanacis Cortex extract and 25 wt % of Puerariae Radix extract, based on the total weight of the complex extract.

Test Example 1

Induction of Adipocyte Differentiation

Preadipocytes 3T3-L1 (KCLB-10092.1, Korean Cell Line Bank) were seeded on a 12-well plate, with $5 \times 10^4$ cells/mL per each well. After adding Dulbecco's modified Eagle's Medium (DMEM; Gibco BRL 11965-084) containing 10% calf serum (Gibco BRL 16170-078), the cells were cultured under the condition of 37° C. and 5% (v/v) $CO_2$ for 2 days. After replacing the medium with DMEM containing 10% (v/v) calf serum, 10 µM dexamethasone (DEX), 0.5 mM 1-methyl-3-isobutylxanthine (IBMX) and 1 µg/mL insulin (differentiation-inducing medium), the cells were further cultured for 2 days under the same condition. Then, after adding DMEM (Sigma Chem. Co., USA) containing 10% (v/v) calf serum and further culturing, the resulting cells were used as control.

Test Example 2

Effect of Each Extract on Lipid Droplet Formation

Each of the *Rehmannia glutinosa*, licorice, *Coicis* Semen, *Hordei* Fructus, *Chaenomelis* Fructus, *Acanthopanacis* Cortex, *Puerariae* Radix and complex extracts prepared in Preparation Example were added to the differentiation-inducing medium at a concentration of 10 ppm to obtain the differentiation-inducing medium containing each extract. Then, differentiation into adipocytes was induced in the same manner as in Test Example 1. The resulting cells were further culturing for 5 days. 2 μM Troglitazone was used as positive control. The differentiated adipocytes were stained with Oil Red O to observe the degree of lipid droplet formation. The result is shown in FIG. 1. Dark spots indicate the presence of lipid droplets. As seen from FIG. 1, all the extracts exhibited excellent effect of promoting lipid droplet formation as compared to the control. In particular, the licorice extract, the *Hordei* Fructus extract and the complex extract showed superior effect.

Test Example 3

Effect of Each Extract on Lipid Droplet Formation

Figure 2:
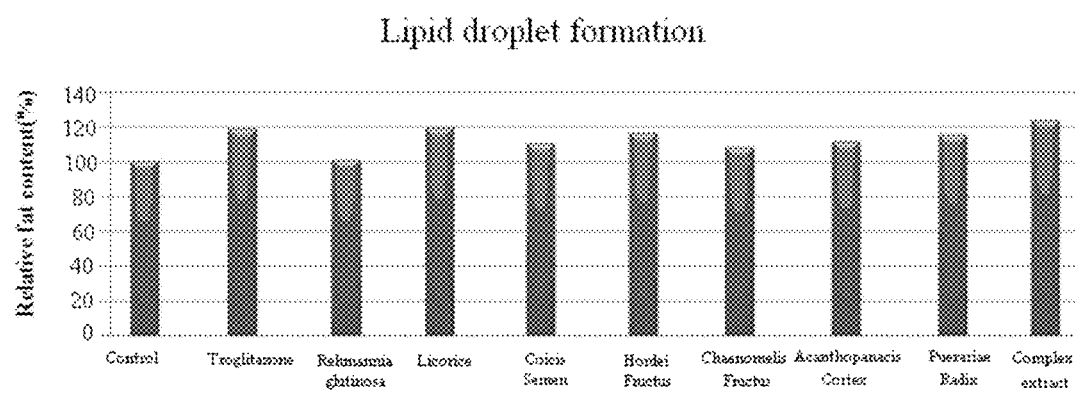
FIG. 2 shows a result of treating 3T3-L1 cells with an extract of *Rehmannia glutinosa*, licorice, Coicis Semen, Hordei Fructus, Chaenomelis Fructus, Acanthopanacis Cortex, Puerariae Radix or a complex extract thereof to induce differentiation, staining with Oil Red O, and measuring absorbance after extracting the Oil Red O dye.

Following Test Example 2, the Oil Red O dye was extracted using propylene glycol (Amresco). Then, absorbance was measured at 500 nm to determine the amount of fat included in the differentiated cells. The fat content was calculated relative to that of the extract-untreated control to determine the degree of differentiation. The result is shown in FIG. 2. As seen from FIG. 2, all the extracts exhibited excellent effect of promoting lipid droplet formation as compared to the control. Notably, the complex extract showed better effect than the positive control Troglitazone.

The effect of promoting lipid droplet formation of the complex extract was calculated relative to those of the *Rehmannia glutinosa*, licorice, *Coicis* Semen, *Hordei* Fructus, *Chaenomelis* Fructus, *Acanthopanacis* Cortex and *Puerariae* Radix extracts based on the result of FIG. 2. The result is shown in Table 1.

TABLE 1

| Extracts | Relative promotion of lipid droplet formation by complex extract (%) |
| --- | --- |
| *Rehmannia glutinosa* | 4110 (approximate 41.1 times) |
| Licorice | 123 (approximate 1.2 times) |
| *Coicis* Semen | 226 (approximate 2.3 times) |
| *Hordei* Fructus | 144 (approximate 1.4 times) |
| *Chaenomelis* Fructus | 298 (approximate 3.0 times) |
| *Acanthopanacis* Cortex | 210 (approximate 2.1 times) |
| *Puerariae* Radix | 151 (approximate 1.5 times) |

As seen from Table 1, the complex extract exhibited very superior effect of promoting lipid droplet formation as compared to the *Rehmannia glutinosa*, licorice, *Coicis* Semen, *Hordei* Fructus, *Chaenomelis* Fructus, *Acanthopanacis* Cortex or *Puerariae* Radix extracts.

Hereinafter, formulation examples of a pharmaceutical composition and a beauty care composition containing a composition comprising an extract of at least one selected from a group consisting of *Rehmannia glutinosa*, licorice, *Coicis* Semen, *Hordei* Fructus, *Chaenomelis* Fructus, *Acanthopanacis* Cortex and *Puerariae* Radix as an active ingredient according to the present disclosure are described in more detail. However, the following examples are for illustrative purposes only and not intended to limit the scope of the present disclosure.

Formulation Example 1

Ointment for External Skin Application

An ointment was prepared according to the composition described in Table 2 according to the commonly employed method.

TABLE 2

| Ingredients | Content (wt %) |
| --- | --- |
| Purified water | balance |
| Glycerin | 8.0 |
| Butylene glycol | 4.0 |
| Liquid paraffin | 15.0 |
| β-Glucan | 7.0 |
| Carbomer | 0.1 |
| *Rehmannia glutinosa*, licorice, *Coicis* Semen, *Hordei* Fructus, *Chaenomelis* Fructus, *Acanthopanacis* Cortex or *Puerariae* Radix extracts | 1.0 |
| Caprylic/capric triglyceride | 3.0 |
| Squalane | 1.0 |
| Cetearyl glucoside | 1.5 |
| Sorbitan stearate | 0.4 |
| Cetearyl alcohol | 1.0 |
| Preservative | adequate |
| Fragrance | adequate |
| Pigment | adequate |
| Beeswax | 4.0 |

Formulation Example 2

Injection

*Rehmannia glutinosa*, licorice, *Coicis* Semen, *Hordei* Fructus, *Chaenomelis* Fructus, *Acanthopanacis* Cortex or *Puerariae* Radix extracts . . . 200 mg Sterile distilled water for injection . . . adequate pH adjuster . . . adequate The above-described ingredients were filled in a 2-mL ampoule according to the commonly employed method.

Formulation Example 3

Nourishing Cream

A nourishing cream was prepared according to the composition described in Table 3 according to the commonly employed method.

TABLE 3

| Ingredients | Content (wt %) |
| --- | --- |
| Purified water | balance |
| Glycerin | 3.0 |
| Butylene glycol | 3.0 |
| Liquid paraffin | 7.0 |
| β-Glucan | 7.0 |
| Carbomer | 0.1 |
| *Rehmannia glutinosa*, licorice, *Coicis* Semen, *Hordei* Fructus, *Chaenomelis* Fructus, *Acanthopanacis* Cortex or *Puerariae* Radix extracts | 3.0 |
| Caprylic/capric triglyceride | 3.0 |
| Squalane | 5.0 |
| Cetearyl glucoside | 1.5 |
| Sorbitan stearate | 0.4 |

TABLE 3-continued

| Ingredients | Content (wt %) |
| --- | --- |
| Polysorbate 60 | 1.2 |
| Preservative | adequate |
| Fragrance | adequate |
| Pigment | adequate |
| Triethanolamine | 0.1 |

Formulation Example 4

Massage Cream

A massage cream was prepared according to the composition described in Table 4 according to the commonly employed method.

TABLE 4

| Ingredients | Content (wt %) |
| --- | --- |
| Purified water | balance |
| Glycerin | 8.0 |
| Butylene glycol | 4.0 |
| Liquid paraffin | 45.0 |
| β-Glucan | 7.0 |
| Carbomer | 0.1 |
| Rehmannia glutinosa, licorice, Coicis Semen, Hordei Fructus, Chaenomelis Fructus, Acanthopanacis Cortex or Puerariae Radix extracts | 1.0 |
| Caprylic/capric triglyceride | 3.0 |
| Beeswax | 4.0 |
| Cetearyl glucoside | 1.5 |
| Sorbitan sesquiolate | 0.9 |
| Vaseline | 3.0 |
| Preservative | adequate |
| Fragrance | adequate |
| Pigment | adequate |
| Paraffin | 1.5 |

Formulation Example 5

Pack

A pack was prepared according to the composition described in Table 5 according to the commonly employed method.

TABLE 5

| Ingredients | Content (wt %) |
| --- | --- |
| Purified water | balance |
| Glycerin | 4.0 |
| Polyvinyl alcohol | 15.0 |
| Hyaluronic acid extract | 5.0 |
| β-Glucan | 7.0 |
| Allantoin | 0.1 |
| Rehmannia glutinosa, licorice, Coicis Semen, Hordei Fructus, Chaenomelis Fructus, Acanthopanacis Cortex or Puerariae Radix extracts | 0.5 |
| Nonyl phenyl ether | 0.4 |
| Polysorbate 60 | 1.2 |
| Preservative | adequate |
| Fragrance | adequate |
| Pigment | adequate |
| Ethanol | 6.0 |

We claim:

1. A method for enhancing skin elasticity of a subject in need therof, comprising:
administering to the subject composition comprising an effective amounts of a *Rehmannia glutinosa* extract, a *Glycyrrhiz uralensis* root extract, a Coicis Semen extract, a Hordei Fructus extract, a Chaenomelis Fructus extract, an Acanthopanacis Cortex extract, and a Puerariae Radix extract, wherein said administering enhances skin elasticity in the subject.

2. The method according to claim 1, wherein the method promotes adipocyte differentiation.

3. The method according to claim 1, wherein the method promotes lipid droplet formation.

4. The method according to claim 1, wherein the *Rehmannia glutinosa* extract, the *Glycyrrhiz uralensis* root extract, the Coicis Semen extract, the Hordei Fructus extract, the Chaenomelis Fructus extract, the Acanthopanacis Cortex extract and the Puerariae Radix extract are administered to the subject in a weight ratio of 20-30:1-10:20-30:1-10:1-10:5-15:20-30.

5. A method for improving skin wrinkles of a subject in need thereof, comprising administering to the subject composition comprising an effective amounts of a *Rehmannia glutinosa* extract, a *Glycyrrhiz uralensis* root extract, a Coicis Semen extract, a Hordei Fructus extract, a Chaenomelis Fructus extract, an Acanthopanacis Cortex extract, and a Puerariae Radix extract, wherein said administering improves skin wrinkles in the subject.

6. The method according to claim 5, wherein the method promotes adipocyte differentiation.

7. The method according to claim 5, wherein the method promotes lipid droplet formation.

8. The method according to claim 5, wherein the *Rehmannia glutinosa* extract, the *Glycyrrhiz uralensis* root extract, the Coicis Semen extract, the Hordei Fructus extract, the Chaenomelis Fructus extract, the Acanthopanacis Cortex extract and the Puerariae Radix extract are administered to the subject in a weight ratio of 20-30:1-10:20-30:1-10:1-10:5-15:20-30.

9. A method for treating skin aging of a subject in need thereof, comprising administering to the subject composition comprising an effective amounts of a *Rehmannia glutinosa* extract, a *Glycyrrhiz uralensis* root extract, a Coicis Semen extract, a Hordei Fructus extract, a Chaenomelis Fructus extract, an Acanthopanacis Cortex extract, and a Puerariae Radix extract, wherein said administering treats skin aging in the subject.

10. The method according to claim 9, wherein the method promotes adipocyte differentiation.

11. The method according to claim 9, wherein the method promotes lipid droplet formation.

12. The method according to claim 9, wherein the *Rehmannia glutinosa* extract, the *Glycyrrhiz uralensis* root extract, the Coicis Semen extract, the Hordei Fructus extract, the Chaenomelis Fructus extract, the Acanthopanacis Cortex extract and the Puerariae Radix extract are administered to the subject in a weight ratio of 20-30:1-10:20-30:1-10:1-10:5-15:20-30.

* * * * *